(12) United States Patent
Angel

(10) Patent No.: US 8,636,009 B2
(45) Date of Patent: Jan. 28, 2014

(54) AIRWAY ASSEMBLY FOR TRACHEAL INTUBATION

(75) Inventor: Luis F. Angel, San Antonio, TX (US)

(73) Assignee: BiO2 Medical, Inc., San Antonio, TX (US)

( * ) Notice: Subject to any disclaimer, the term of this patent is extended or adjusted under 35 U.S.C. 154(b) by 1354 days.

(21) Appl. No.: 10/569,397

(22) PCT Filed: Aug. 23, 2004

(86) PCT No.: PCT/US2004/027285
§ 371 (c)(1),
(2), (4) Date: Nov. 13, 2006

(87) PCT Pub. No.: WO2005/018713
PCT Pub. Date: Mar. 3, 2005

(65) Prior Publication Data
US 2007/0055343 A1    Mar. 8, 2007

Related U.S. Application Data

(60) Provisional application No. 60/497,140, filed on Aug. 22, 2003.

(51) Int. Cl.
*A61M 16/00* (2006.01)
(52) U.S. Cl.
USPC .................................... 128/207.14; 128/898
(58) Field of Classification Search
USPC ............. 128/200.24, 200.26, 204.18, 205.18,
128/207.14–207.17; 604/77, 264, 96.01,
604/103, 103.09, 104, 523, 524, 526, 527
See application file for complete search history.

(56) References Cited

U.S. PATENT DOCUMENTS

| | | | |
|---|---|---|---|
| 3,616,799 A | 11/1971 | Sparks | |
| 3,709,227 A | 1/1973 | Hayward | |
| 3,769,983 A | 11/1973 | Merav | |
| 3,995,643 A | 12/1976 | Merav | |
| 4,141,364 A * | 2/1979 | Schultze | 128/207.15 |
| 4,987,895 A | 1/1991 | Heimlich | |
| 5,041,093 A * | 8/1991 | Chu | 604/104 |
| 5,201,757 A | 4/1993 | Heyn et al. | |
| 5,250,070 A * | 10/1993 | Parodi | 606/194 |
| 5,494,029 A * | 2/1996 | Lane et al. | 128/207.15 |
| 5,512,055 A | 4/1996 | Domb et al. | |

(Continued)

*Primary Examiner* — Clinton T Ostrup
*Assistant Examiner* — LaToya M Louis
(74) *Attorney, Agent, or Firm* — David G. Rosenbaum; J. Peter Paredes; Rosenbaum IP

(57) ABSTRACT

In some embodiments, an airway assembly may be used in a procedure that requires tracheal intubation. The airway assembly may include a first conduit, a sleeve, and a stent. The first conduit and the sleeve may be relatively flexible, facilitating insertion of the airway assembly in a body lumen (e.g., an air passage way). The first conduit may function to deliver gases (e.g., air) to the body lumen and consequently the patient. The first conduit may be positioned in the sleeve during use. The sleeve may be removably coupled to the first conduit. In certain embodiments, a sleeve may function to inhibit a stent from expanding until desired. In some embodiments, an elongated member may be positionable in the first conduit. The elongated member may be configurable to substantially retain a new shape upon deformation. The stent may be coupled towards the distal end of the first conduit. The stent may function to inhibit the body lumen from collapsing. In certain embodiments, a stent may function to inhibit the body lumen from collapsing without exerting unnecessary outward pressures on the inner surface of the body lumen.

7 Claims, 1 Drawing Sheet

(56) References Cited

U.S. PATENT DOCUMENTS

| | | |
|---|---|---|
| 5,607,386 A * | 3/1997 | Flam .............................. 600/120 |
| 5,749,883 A * | 5/1998 | Halpern ........................ 606/159 |
| 5,762,638 A | 6/1998 | Shikani et al. |
| 5,791,341 A | 8/1998 | Bullard |
| 5,803,080 A | 9/1998 | Freitag |
| 5,893,868 A | 4/1999 | Hanson et al. |
| 6,585,639 B1 | 7/2003 | Kotmel et al. |
| 6,668,832 B2 * | 12/2003 | Hipolito et al. .......... 128/207.14 |
| 6,830,575 B2 * | 12/2004 | Stenzel et al. ................. 606/108 |
| 2003/0135256 A1 * | 7/2003 | Gallagher et al. ........... 623/1.11 |
| 2004/0020492 A1 * | 2/2004 | Dubrul et al. ............ 128/207.18 |
| 2004/0255951 A1 * | 12/2004 | Grey ........................ 128/207.14 |
| 2005/0049577 A1 * | 3/2005 | Snell et al. .................... 604/544 |
| 2005/0205097 A1 | 9/2005 | Kyle, Jr. |

\* cited by examiner

AIRWAY ASSEMBLY FOR TRACHEAL INTUBATION

PRIORITY CLAIM

This application claims priority to PCT Patent Application No. PCT/US04/27285 entitled "AIRWAY ASSEMBLY FOR TRACHEAL INTUBATION" filed on Aug. 23, 2004, which claims priority to Provisional Patent Application No. 60/497,140 entitled "AIRWAY ASSEMBLY FOR TRACHEAL INTUBATION" filed on Aug. 22, 2003, each of which is incorporated herein by reference.

BACKGROUND OF THE INVENTION

1. Field of the Invention

The present invention relates to systems for providing gases (e.g., air) to a patient through a body lumen. Specific embodiments of the invention relate to endotracheal intubation.

2. Description of the Relevant Art

An endotracheal tube generally comprises a cylindrical tube used as an air passage to administer oxygen, anesthetic gases and medications directly to the patient. The cylindrical tube terminates in an open distal end configured for insertion into the trachea and has an opposite open proximal end configured to be coupled to a gas source. The endotracheal tube typically has an inflatable cuff on the exterior of the cylindrical tube for forming a seal with the interior walls of the trachea. The cuff functions to occlude the trachea, which protects the trachea and lungs against aspiration of foreign substances. In particular, food, foreign bodies or digestive system contents are prevented from entering the lungs. The endotracheal tube is used primarily in surgery and in the intensive care units in patients requiring mechanical ventilation, but is also frequently used in emergency rooms and emergency in-the-field situations.

The use of tracheal tubes in the medical world is widespread both in hospitals and for at home care. Tracheal tubes are used for holding weak airways open as well as in intubation for mechanical ventilation and the direct application of oxygen therapy. Constant monitoring of the patency of these tubes is required due to the immense risks associated with failure. The mechanics of tracheal tubes in artificial ventilation are particularly important to control for patients with conditions such as quadriplegia, degenerative muscular or intellectual disorders. These patients may be unable to understand or express their distress at pain sensations associated with cuff pressure or loss of air movement.

There are two main types of intubation using tracheal tubes. Either the tube is inserted through the nose or mouth (called endotracheal intubation) and down the airway, or through an external hole in the throat called a tracheal stoma. The first of these is more common, and is used frequently in acute intensive care, operating rooms to provide anesthesia or emergency applications. Direct tracheal intubation (tracheostomy) is used when endotracheal intubation is unfeasible due to medical indications or to provide chronic mechanical ventilation to patients that require ventilatory support to breathe. This may occur in an emergency situation where the airway may not be cleared in time or for long-term patients whose trachea is damaged such that it is in danger of collapse.

In surgical procedures requiring general anesthesia, the patient is rendered unconscious by administration of anesthetic agents including drugs and/or gases. The patient is also given a muscle relaxant/paralyzing agent to minimize the patient's gagging response to the insertion of the endotracheal tube. A laryngoscope is placed in the mouth of the patient. The blade portion of the laryngoscope is used to push the tongue laterally and the intubating practitioner applies a lifting force to the laryngoscope handle in order to visualize the anatomical structures of the mouth and airway. A specific target area of the tracheal tube is the glottis, which is the opening between the vocal cords and the inlet to the trachea. The distal end of the endotracheal tube is inserted into the glottis and the inflatable cuff (balloon) is filled with air to create an airtight seal between the cuff walls and the interior walls of the trachea. This airtight seal allows for delivery of the oxygen and anesthetic gases with positive pressure directly to the air passages below the tip and the balloon.

Endotracheal intubation is one of the most common procedures performed by physicians in hospitals. Patients in the intensive care units on mechanical ventilation require this kind of procedure to have access to the airways and to have mechanical ventilation. However this life saving procedure is sometimes difficult in complicated airways. Complications may include aspiration pneumonias secondary to cuff leaks and poor clearance of secretions, as well as, difficulties with ventilation due to high pressures and in some patients with post-intubation tracheal stenosis (narrowing of the trachea in the area were the cuff of the endotracheal tube is making contact with the tracheal mucosa).

Concern about complications stemming from the use of artificial airways has been evident since these devices were first introduced into clinical practice. When MacEwen successfully performed transoral endotracheal intubation in 1878 for the relief of upper airway obstruction, he recognized the potential for complications of this procedure. His report of 4 cases includes description of adverse effects associated with the use of endotracheal tubes (ETTs), including patient discomfort, cough, mucosal congestion, and glottic edema. MacEwen's first patient actually experienced no complications from the procedure: "After the operation was finished, the tube was withdrawn, it having acted throughout without the slightest hitch."

There are many long and short term problems associated with the use of tracheal tubes. Long-term problems include stenosis of the mucosal lining of the trachea, and permanent scarring of the airway. Stenosis, the narrowing of the airway, is caused by the pressure of the tube on the inside of the trachea, wearing away the lining and allowing bacteria to build. Scarring arises from undiagnosed or untreated tracheal stenosis as well as frequent or traumatic tube changes. This further exacerbates the problem due to hardening and swelling of the airway making patency harder to achieve.

Short-term problems can either arise through normal operation of the ventilator or tube or from complications and failures in these mechanisms. During normal usage, secretions accumulate in the lungs of the patient due to the steady flow of mucus from the distal small airways into the larger and more proximal bronchi and trachea. In patients that are intubated, this fluid must be suctioned out of the lungs to prevent muccus plugging, lung collapse and pneumonia.

The pressure limited tracheal tube cuff (PLC) (Young et al., 1999) effectively eliminates the leakage of secretions past the cuff and into the lungs. These leakages occur in between 20% and 60% of all ventilated patients and may have a mortality rate due to pneumonia and other complications as high as 25%. The apparatus involved is designed to eliminate longitudinal creases, which allow fluid to channel past the tube cuff, and was found to be very effective in trials. Secretions developed by the lungs themselves as a reaction to the foreign body will still require suctioning but this will be much reduced.

Air leaks occur when the tube is not in full contact with the walls of the airway. This limits the effectiveness of the tube, particularly for mechanically ventilated patients who often require the full predetermined volume of air to maintain adequate ventilation and acceptable oxygen levels due to a decreased capacity to absorb oxygen. Air leaks are common due to positional changes of the patient that can dramatically change both the contact area of the tube and the pressure upon the tracheal walls. This increase in pressure due to changes in patient position is the primary cause of mucosal ulceration and stenosis.

While some of the adverse events associated with endotracheal intubation are inherent consequences of airway instrumentation, rather than true complications, most of the complications are avoidable, and a great deal of research has been published on the recognition, management, and avoidance of these problems. There is a need, however, for an artificial airway system, which may assist in inhibiting many of the complications associated with current technologies.

SUMMARY

Airway assemblies may be used in situations for anyone who may require assistance in breathing. Examples of surgical procedures may include ventilating, suctioning fluid, observing, treating and/or obtaining biological material from within the patient. Instruments to be inserted into an air passage of a patient include, but are not limited to, endoscopes, biopsy needles, forceps, cutters and/or large volume suction tubes.

In some embodiments, an airway assembly as described herein may be inserted through an opening (e.g., artificially induced) in a body lumen (e.g., in a tracheostomy). Tracheotomy is a surgical procedure that is usually done in the operating room under general anesthesia, although it may be performed during emergency situations without the benefit of general anesthesia. A tracheotomy is an incision into the trachea (windpipe) that forms a temporary or permanent opening which is called a tracheostomy. Sometimes the terms "tracheotomy" and "tracheostomy" are used interchangeably. The opening, or hole, is called a stoma. The incision usually runs from the second to the fourth tracheal ring. A tube is inserted through the opening to allow passage of air and removal of secretions. Instead of breathing through the nose and mouth, a subject will now breath through the tracheostomy tube. In some embodiments described herein, an airway assembly may be inserted through an opening (e.g., naturally occurring) in a body lumen.

An airway assembly may include a first conduit, a sleeve, and a stent. In some embodiments, the airway assembly may include an elongated member. The elongated member may be positionable in the first conduit. The first conduit may function to deliver gases (e.g., air) to the body lumen and/or any lumen/organ coupled to the body lumen. The stent may be coupled toward the distal end of the first conduit. The stent may function to inhibit collapse of the body lumen. A first conduit may be positionable in the sleeve.

In some embodiments, an airway assembly may include a first conduit formed from a flexible material. Forming the first conduit from a flexible material may allow for easier insertion of the airway assembly into a body lumen. A stent may be formed from a material which is less flexible than the first conduit. Forming the stent from a material less flexible than the first conduit may allow the stent to assist in inhibiting collapse of the body lumen during use.

Using a stent to inhibit collapse of the body lumen may have certain advantages over such current practices and technologies such as inflatable cuffs. Stents may function to keep open the body lumen without exerting significant outward pressure on the inner surface of the body lumen. Current technologies such as inflatable cuffs tend to exert outward pressure on the inner surface of the body lumen. Exerting outward pressure on the inner surface of a body lumen may lead to complications later upon extraction of an airway assembly. Other problems with current technologies include the ulceration and stenosis of the trachea below the glottis. Ulceration and stenosis of the trachea below the glottis is caused by high levels of sustained tracheal pressure that wear down the mucosal lining, leading to infection and scarring. Another problem is decreased effectiveness of ventilation due to a large air leak around the cuff.

In some embodiments, an airway assembly may include an elongated member. The elongated member may be positionable in the airway assembly. The elongated member may function to facilitate insertion of the airway assembly in a body lumen.

In some embodiments, one or more portions of an elongated member may be coupled to a first conduit. The elongated member may be removably attached to the first conduit, allowing the elongated member to be removed/attached to the first conduit before, during, and/or after insertion of an airway assembly.

In certain embodiments, an airway assembly may include a sleeve. A portion of a first conduit may be positionable in the sleeve. The sleeve may serve multiple functions. Portions of the sleeve may be flexible to facilitate insertion of the airway assembly into a body lumen. An outer surface of the sleeve may include a layer or coating of a material having a low coefficient of friction to facilitate insertion of the sleeve into the body lumen.

In some embodiments, a sleeve may be configured to be removable during use. For example, the sleeve may be configured to be removed before and/or after insertion of an airway assembly into a body lumen. In certain embodiments, a sleeve may be configured to "peel" away from a first conduit during use. The sleeve may inhibit expansion of a stent until desirable.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
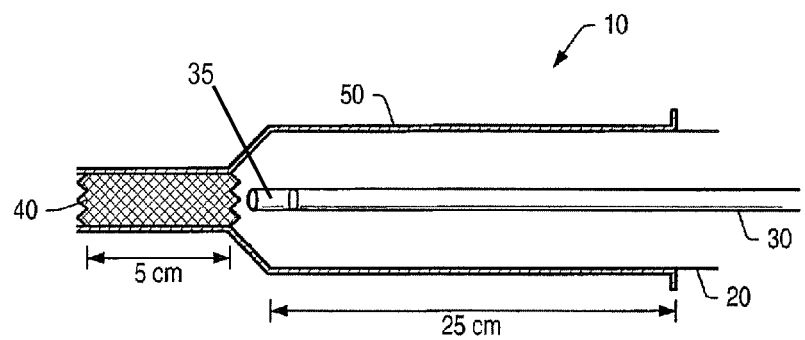
FIG. 1 depicts a cross sectional view of an embodiment of an artificial airway assembly including a sleeve.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Referring to the drawings an airway assembly is designated generally by reference number 10. Airway assembly 10 may be used in situations for anyone who may require assistance in breathing. Air-way assembly 10 may be used in a surgical procedure that requires administration of gases. Examples of surgical procedures may include ventilating, suctioning fluid, observing, treating and/or obtaining biological material from within the patient. Instruments that may be inserted into an air passage of a patient include, but are not limited to, endoscopes, biopsy needles, forceps, cutters and/or large volume suction tubes.

Airway assembly 10 may be made of various materials including, but not limited to, metals, metal alloys, silicon, plastic, polymers, ceramics and combinations thereof. Some airway assemblies may include components made of materials that can be autoclaved and/or chemically sterilized. Some components of an airway assembly may be formed of materials unable to be autoclaved and/or chemically sterilized. Components unable to be autoclaved and/or chemically sterilized may be made of sterile materials and placed in working relation to other sterile components during assembly of an airway assembly. In some embodiments, an entire airway assembly may be made of materials that can be autoclaved and/or chemically sterilized so that the airway assembly is a reusable instrument. In other airway assembly embodiments, all or selected components of the airway assembly may be made of sterile, disposable materials so that the selected components of the airway assembly are designed for single use.

In some embodiments, airway assembly 10 may include a first conduit 20. Airway assembly 10 may include an elongated member 30. Airway assembly 10 may include a stent 40. Airway assembly 10 may include a sleeve 50. Airway assembly 10 may be inserted in an air passage of a patient. Elongated member 30 may be positionable in first conduit 20. Stent 40 may be positioned approximate the distal end of first conduit 20.

In certain embodiments, stent 40 may be coupled to first conduit 20. The proximal end of stent 40 may be coupled to the distal end of first conduit 20. In some embodiments, a portion of stent 40 may be coupled to a portion of the outer surface of first conduit 20. In some embodiments, a portion of stent 40 may be coupled to a portion of the inner surface of first conduit 20. Stent 40 may be coupled to first conduit 20 using, for example, biologically inactive adhesives. In some embodiments, stent 40 may be formed as part of first conduit 20.

In certain embodiments, first conduit 20 may function to deliver gases (e.g., air, medicinal gases) to a patient. In some embodiments, first conduit 20 may function to deliver fluids (e.g., air). Fluids may include, but are not limited to, gases and liquids. Gases may include air, oxygen, and/or medicinal gases (e.g., analgesics). In some embodiments, first conduit 20 may function to remove fluids from the body lumen. An apparatus inserted in an air passage may provide for removal of bodily fluids, such as blood, mucus and gastric fluids. U.S. Pat. No. 5,143,062 to Peckham, describes an endotracheal tube that may suction a patient's secretions.

During some surgical procedures, the proximal end of first conduit 20 may be coupled to a supply line. The supply line may allow gases (e.g., air), rinse fluid, medication or other fluid to be inserted into a region beyond the distal end of airway assembly 10. If needed, suction distal to airway assembly 10 may be provided through first conduit 20 when first conduit 20 is coupled to a pressure reduction source (e.g., vacuum pump or aspirator).

In some embodiments, first conduit 20 may be formed from a flexible material. Forming first conduit 20 from a flexible material may allow for easier insertion of airway assembly 10 into a body lumen. Stent 40 may be formed from a material which is less flexible than first conduit 20. Forming stent 40 from a material less flexible than first conduit 20 may allow stent 40 to assist in inhibiting collapse of the body lumen during use.

Portions of first conduit 20 may be flexible to facilitate insertion of airway assembly 10 into a body lumen of a patient. An outer surface of first conduit 20 may include a layer or coating of a material having a low coefficient of friction to facilitate insertion of the first conduit into the body lumen.

A portion of first conduit 20 may include a layer or coating of a material on an inner surface that facilitates insertion of instruments into the first conduit. For example, the inner surface of first conduit 20 may include a fluorine containing resin layer (e.g., TEFLON®) or other material with a low coefficient of friction.

A portion of first conduit 20 may be sized to fit within an air passage of a patient. The first conduit may be cylindrical in shape. First conduit 20 may have a diameter between about 3 mm and about 25 mm. In some embodiments, first conduit 20 may have a diameter between about 10 mm and about 17 mm. First conduits having larger or smaller diameters may be used to accommodate specific requirements of a patient.

A stent is a resilient device often used in anchoring vascular grafts and for supporting body openings during the grafting of vessels and tubes of the body during surgery. Also, stents are frequently used, without grafts, for supporting luminal patency. More recently, artificial (woven or non-woven polymeric) grafts have been used in cardiac, vascular, and nonvascular applications to provide extra support. Moreover, stents may be separated into self-expanding and plastically deformed stents. A self-expanding stent is deployed by its self-expanding resilience. A plastically deformed stent is deployed by plastic deformation of the constituent material with a balloon or other such dilating instrument.

Using stent 40 to inhibit collapse of the body lumen may have certain advantages over such current practices and technologies such as inflatable cuffs. Stents may include commercially available stents and/or stents designed specifically for the purposes described herein. Stents 40 may function to keep open the body lumen without exerting significant outward pressure on the inner surface of the body lumen. Current technologies such as inflatable cuffs tend to exert outward pressure on the inner surface of the body lumen. Exerting outward pressure on the inner surface of a body lumen may lead to complications later upon extraction of an airway assembly. Complications may result due to pressure exerted on the inner surface of a body lumen stretching or extending the portion of the body lumen surrounding the point of contact between the body lumen and the inflatable cuff. Upon extraction of an airway assembly employing an inflatable cuff from a body lumen, the body lumen may potentially collapse upon itself blocking the lumen.

Current technologies such as inflatable cuffs may have a tendency to malfunction. For example, inflatable cuffs may lose pressure over time. Upon a certain amount of loss of pressure an inflatable cuff may allow fluids (e.g., mucus) to drain. Loss of pressure in an inflatable cuff may be a problem especially in instances when an airway assembly must be left in a patient for an extended period of time. Stent 40 may assist in circumventing this problem in that the stent does not require inflation and therefore is less likely to allow the drainage of fluids.

In some embodiments, stent 40 may include expandable stents. Expandable stents may include, but are not limited to, self-expanding stents and assisted expanding stents. Assisted expanding stents may be expanded after insertion with the assistance of a balloon. A stent may be inhibited from expanding during insertion and upon positioning the stent within an airway the stent may be allowed/assisted to expand.

In some embodiments, stent 40 may include a covering or layer of material surrounding the stent or at least a majority of the stent. The material may assist in preventing drainage of fluids and air leakage during mechanical ventilation. The material may be coupled to stent 40 in any way known to one skilled in the art.

Figure 2:
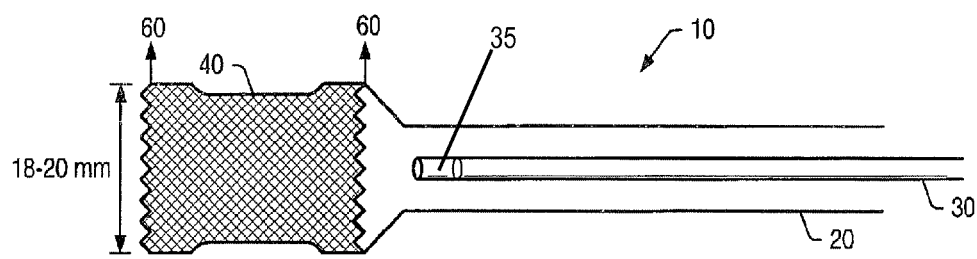
FIG. 2 depicts a cross sectional view of an embodiment of an artificial airway assembly without a sleeve.

In certain embodiments, airway assembly 10 may include one or more markers 60. Markers 60 may assist a user in assessing a relative position of at least a portion of airway assembly 10 in a body lumen during use. In some embodiments, markers 60 may be positioned at approximately the distal and proximal ends of stent 40 as depicted in FIG. 2. Positioning markers 60 as depicted in FIG. 2 may advantageously allow a user (e.g., a doctor, nurse, or technician) to monitor the position of stent 40 during and/or after insertion. The capability to monitor the position of stent 40 over time helps ensure that the stent has not shifted potentially causing problems. Markers 60 may include, but are not limited to, radio-opaque markers In certain embodiments, stent 40 may be sized to fit within an air passage of a patient upon expansion. Stent 40 may be approximately cylindrical in shape. Stent 40 may have a diameter between about 3 mm and about 25 mm. In some embodiments, stent 40 may have a diameter between about 10 mm and about 17 mm. In some embodiments, stent 40 may have a diameter between about 18 mm and about 20 mm as depicted in FIG. 2. Stent 40 may have a length between about 1 cm and about 12 cm. In some embodiments, stent 40 may have a length between about 3 cm and about 8 cm. In some embodiments, stent 40 may have a length between about 4 cm and about 6 cm as depicted in FIG. 1. Stents having larger or smaller diameters and/or lengths may be used to accommodate specific requirements of a patient.

In some embodiments, airway assembly 10 may include elongated member 30. Elongated member 30 may be positionable in airway assembly 10. Elongated member 30 may include an intubation stylet. Elongated member 30 may comprise a light 35, as illustrated in FIGS. 1 and 2. Elongated member 30 may be slightly flexible. Elongated member 30 may be formed from a substance allowing for its deformation into various different shapes. Upon deformation of elongated member 30, the elongated member may substantially retain the new shape. Elongated member 30 may be positioned in first conduit 20 before insertion of airway assembly 10 into a body lumen. Once elongated member 30 is positioned in first conduit 20, elongated member 30 may function to allow for the deformation of airway assembly 10. Deformation of airway assembly 10 may facilitate insertion of airway assembly 10 into a body lumen. Use of elongated member 30 may allow at least portions of airway assembly 10 to be formed from relatively more flexible materials. Relatively more flexible materials may inhibit airway assembly 10 from retaining a new shape upon deformation without the use of elongated member 30.

In some embodiments, one or more portions of elongated member 30 may be coupled to first conduit 20. Elongated member 30 may be removably attached to first conduit 20, allowing the elongated member to be removed/attached to the first conduit before, during, and/or after insertion of airway assembly 10. Elongated member 30 may be positioned in first conduit 20 before, during, and/or after insertion of airway assembly 10 while remaining unattached to airway assembly 10.

Portions of elongated member 30 may be flexible to facilitate insertion into first conduit 20. An outer surface of elongated member 30 may include a layer or coating of a material having a low coefficient of friction to facilitate insertion of the elongated member into first conduit 20.

In certain embodiments, airway assembly 10 may include sleeve 50. A portion of first conduit 20 may be positionable in sleeve 50. Sleeve 50 may serve multiple functions. Portions of sleeve 50 may be flexible to facilitate insertion of airway assembly 10 into a body lumen. An outer surface of sleeve 50 may include a layer or coating of a material having a low coefficient of friction to facilitate insertion of the sleeve into the body lumen. When sleeve 50 is employed as part of airway assembly 10, it may not be necessary to include a layer or coating of a material having a low coefficient of friction to the outer surface of first conduit 20. In certain embodiments, an inner surface of sleeve 50 may include a layer or coating of a material having a relatively higher coefficient of friction to inhibit movement of sleeve 50 relative to first conduit 20 during use (e.g., during insertion).

In some embodiments, sleeve 50 may function to apply pressure to stent 40 so as to assist in inhibiting movement of stent 40 relative to first conduit 20. In some embodiments, sleeve 50 may function to inhibit premature expansion of stent 40 during use. Sleeve 50 may inhibit premature expansion of stent 40 by applying pressure to the stent. Upon proper positioning of airway assembly 10, and more specifically stent 40, within a body lumen sleeve 50 may be removed. Removal of sleeve 50 may allow the expansion of stent 40 within the body lumen. In some embodiments, only a portion of sleeve 50 may be removed and/or repositioned allowing stent 40 to expand with or without assistance.

In certain embodiments, sleeve 50 may compress and/or restrict a diameter of stent 40 during use. Sleeve 50 may compress and/or restrict a diameter of stent 40 during use such that the diameter of at least portions of the stent are relatively smaller than a diameter of first conduit 20. In some embodiments, sleeve 50 may function to compress stent 40 such that the distal end of the stent is tapered. A tapered distal end of stent 40 may facilitate insertion of airway assembly 10.

In some embodiments, sleeve 50 may be formed from a substance allowing for its deformation into various different shapes. Upon deformation of sleeve 50, the sleeve may substantially retain the new shape. Sleeve 50 may function to allow for the deformation of airway assembly 10. Deformation of airway assembly 10 may facilitate insertion of airway assembly 10 into a body lumen. Use of sleeve 50 may allow at least portions of airway assembly 10 to be formed from relatively more flexible materials. Relatively more flexible materials may inhibit airway assembly 10 from retaining a new shape upon deformation without the use of sleeve 50.

In some embodiments, sleeve 50 may be configured to be removable during use. For example, sleeve 50 may be configured to be removed after insertion of airway assembly 10 into a body lumen. In certain embodiments, sleeve 50 may be configured to "peel" away from first conduit 20 during use. Sleeve 50 may be configured to peel away from first conduit 20 after airway assembly 10 has been inserted into a body lumen. In some embodiments, sleeve 50 may include a line of detachment. The line of detachment may facilitate peeling away sleeve 50 during use. The line of detachment may extend the majority or all of the length of sleeve 50. The line of detachment may be perforated. The line of detachment may be simply scored.

In some embodiments, sleeve 50 may be removed without the use of a line of detachment. For example sleeve 50 may be removed from airway assembly 10 by moving the sleeve relative to the outer surface of first conduit 20. Removing sleeve 50 by sliding the sleeve off as described may result in the sleeve being removed in a relatively undamaged state.

Figure 3:
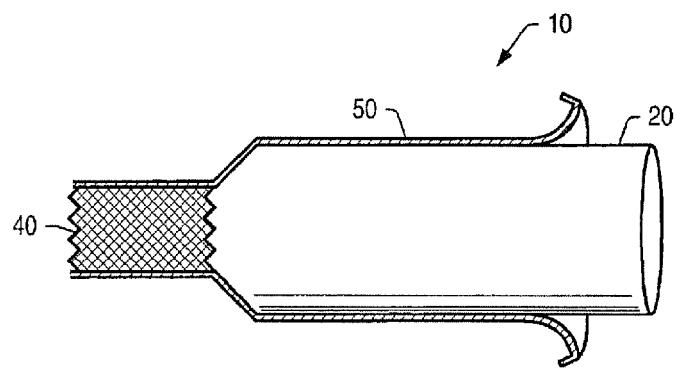
FIG. 3 depicts a cross sectional view of an embodiment of an artificial airway assembly wherein a sleeve is being peeled away from a first conduit.

In some embodiments, sleeve 50 may include a grip or a portion facilitating the action of grasping and removing the sleeve from airway assembly 10. The grip may include, as a non-limiting example, a proximal portion of sleeve 50 wherein the proximal portion is curled slightly outward or inward to provide a protruding "lip". The lip may be used as a grip by a user to more easily grasp sleeve 50 and remove the sleeve. An example of a lip is depicted in FIG. 1 and FIG. 3.

In certain embodiments, airway assembly 10, including sleeve 50, may be inserted in an air passage during use. FIG. 1 depicts airway assembly 10, including sleeve 50. When stent 40 has been determined to be approximately properly positioned within the air passage, sleeve 50 may be totally or at least partially retracted/removed. In some embodiments, one or more markers 60 may be employed to assess the position of stent 40. Upon retraction of the distal end of sleeve 50 beyond the distal end of stent 40, the sleeve will no longer inhibit expansion of the stent. In an embodiment including a self-expanding stent, upon retraction of sleeve 50 the stent will automatically expand to conform to the body lumen the stent is currently positioned within as depicted in FIG. 2. In some embodiments including an assisted expanding stent (e.g., a balloon-expandable stent), upon retraction of sleeve 50 a stent expansion assistance device may be inserted through first conduit 20 to assist in expanding stent 40.

In some embodiments, one or more portions of an airway assembly may include biologically active compounds. Biologically active compounds (e.g., medicinal compounds, pharmaceutical compounds) may be impregnated within the materials forming one or more of the portions of the airway assembly and/or the biologically active compounds may be part of a coating applied to one or more of the portions of the airway assembly.

Further modifications and alternative embodiments of various aspects of the invention will be apparent to those skilled in the art in view of this description. Airway assemblies may be modified to operate in other areas of a patient in which it is desired to separate a first region from a second region by a seal formed in a passage of the patient. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for endotracheal intubation, the method comprising the steps of:
    inserting at least a distal end of an airway assembly in an air passage selected from one of the trachea, right bronchus or left bronchus of a patient, wherein the airway assembly comprises:
        a first elongated tubular conduit with a proximal end and a distal end, wherein the distal end of the first elongated tubular conduit is positionable within one of the trachea, right bronchus or left bronchus of the patient and the proximal end of the first elongated tubular conduit remains outside the patient's body, and wherein the first elongated tubular conduit is configurable to deliver gas to the patient's lungs;
        a stent having at least a proximal end that is fixedly coupled to the distal end of the first elongated tubular conduit, wherein the stent is formed from a material that is less flexible than the first tubular conduit and is configurable to expand into contact with and to inhibit collapse of at least a portion of the trachea, right bronchus or left bronchus; and
        a sleeve, wherein at least a portion of the distal end of the first elongated tubular conduit and at least a portion of the stent are positionable in the sleeve, and wherein the sleeve inhibits the stent from expanding until the sleeve is removed from the stent;
    retracting at least a portion of the sleeve substantially surrounding the stent; and
    delivering fluids through the proximal end of the first elongated tubular conduit into the air passage.

2. The method of claim 1, further comprising the step of: positioning at least a portion of a stent expansion device in the stent.

3. The method of claim 1, further comprising the step of: inserting the distal end of the airway assembly through a non-natural opening in the air passage.

4. The method of claim 1, further comprising the step of: inserting the distal end of the airway assembly through a natural opening in the air passage.

5. The method of claim 1, further comprising the steps of: positioning at least a portion of a stent expansion device in the stent; and expanding the stent.

6. The method of claim 1, further comprising the step of: positioning an elongated member in the first elongated tubular conduit, wherein the elongated member is deformable from an original shape into a new shape and substantially retains the new shape upon deformation of the elongated member.

7. The method of claim 1, further comprising the steps of: positioning an elongated member in the first elongated tubular conduit, wherein the elongated member is deformable from an original shape into a new shape and substantially retains the new shape upon deformation of the elongated member; and deforming the elongated member so as to facilitate insertion of the distal end of the first elongated tubular conduit in the air passage.

\* \* \* \* \*